US012630508B2

(12) United States Patent
Namba et al.

(10) Patent No.: US 12,630,508 B2
(45) Date of Patent: May 19, 2026

(54) METHOD FOR MANUFACTURING HETEROCYCLE-CONTAINING AMINO ACID COMPOUND

(71) Applicants: Tokushima University, Tokushima (JP); AICHI STEEL CORPORATION, Tokai (JP)

(72) Inventors: Kosuke Namba, Tokushima (JP); Akane Mera, Tokai (JP); Motofumi Suzuki, Tokai (JP)

(73) Assignees: TOKUSHIMA UNIVERSITY, Tokushima (JP); AICHI STEEL CORPORATION, Tokai (JP)

( * ) Notice: Subject to any disclaimer, the term of this patent is extended or adjusted under 35 U.S.C. 154(b) by 539 days.

(21) Appl. No.: 18/261,383

(22) PCT Filed: Oct. 8, 2021

(86) PCT No.: PCT/JP2021/037366
§ 371 (c)(1),
(2) Date: Jul. 13, 2023

(87) PCT Pub. No.: WO2022/153626
PCT Pub. Date: Jul. 21, 2022

(65) Prior Publication Data

US 2024/0092734 A1 Mar. 21, 2024

(30) Foreign Application Priority Data

Jan. 15, 2021 (JP) ................................ 2021-005265

(51) Int. Cl.
*C07D 207/16* (2006.01)

(52) U.S. Cl.
CPC ................................ *C07D 207/16* (2013.01)

(58) Field of Classification Search
CPC ................................................... C07D 207/16
See application file for complete search history.

(56) References Cited

U.S. PATENT DOCUMENTS

| | | | | |
|---|---|---|---|---|
| 10,638,758 | B2 * | 5/2020 | Namba | A01N 43/36 |
| 11,939,290 | B2 * | 3/2024 | Namba | C07F 15/02 |
| 2010/0256395 | A1 | 10/2010 | Namba et al. | |
| 2018/0303093 | A1 | 10/2018 | Namba et al. | |
| 2021/0253522 | A1 | 8/2021 | Namba et al. | |

FOREIGN PATENT DOCUMENTS

| | | | |
|---|---|---|---|
| JP | 2006232733 | A | 9/2006 |
| JP | 6347396 | B2 | 6/2018 |
| JP | 6744530 | B2 | 8/2020 |
| WO | 2008059782 | A1 | 5/2008 |
| WO | 2017082111 | A1 | 5/2017 |
| WO | 2020045247 | A1 | 3/2020 |

OTHER PUBLICATIONS

International Search Report dated Dec. 14, 2021 for International Application No. PCT/JP2021/037366, 5 pages including English translation.

Extended European Search Report issued in corresponding European Patent Application No. 21919517.9 dated Feb. 14, 2025, 9 pages.

* cited by examiner

*Primary Examiner* — Golam M Shameem
(74) *Attorney, Agent, or Firm* — MH2 Technology Law Group, LLP

(57) ABSTRACT

Provided is a simple method for producing a heterocycle-containing amino acid compound. A heterocycle-containing amino acid compound is produced by a method comprising step A of reacting a compound represented by the following formula (2) or a salt thereof:

(2)

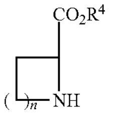

wherein $R^4$ is a hydrogen atom or a carboxyl-protecting group, and n is an integer of 1 to 3, acrolein, a cyanating agent, and a compound represented by the following formula (3) or a salt thereof:

(3)

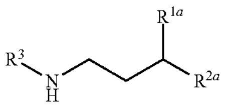

wherein $R^{1a}$ is a hydrogen atom or $CO_2R^{1b}$, $R^{1b}$ is a hydrogen atom or a carboxyl-protecting group, $R^{2a}$ is a hydrogen atom or $OR^{2b}$, $R^{2b}$ is a hydrogen atom or a hydroxyl-protecting group, and $R^3$ is a hydrogen atom or an amino-protecting group.

9 Claims, No Drawings

METHOD FOR MANUFACTURING HETEROCYCLE-CONTAINING AMINO ACID COMPOUND

CROSS-REFERENCE TO RELATED APPLICATIONS

This application is a national stage application of PCT/JP2021/037366 filed 8 Oct. 2021, which claims priority to Japanese Patent Application No. 2021-005265 filed 15 Jan. 2021, the entire disclosures of which are herein incorporated by reference.

TECHNICAL FIELD

The present invention relates to, for example, a method for producing a heterocycle-containing amino acid compound.

BACKGROUND ART

Various trace metal elements are involved in the growth of plants and the maintenance of their functions, and deficiencies of these trace metal elements make normal plant growth impossible. For example, iron is an element necessary for respiration, photosynthesis, DNA synthesis, and the like, and is an active center metal of, in particular, an enzyme that is essential for biosynthesis of chlorophyll. Accordingly, iron deficiency causes chlorosis (iron deficiency chlorosis), in which the leaves turn yellow.

On the other hand, poor soils, which are considered unsuitable for agriculture, account for about 67% of the total land area in the world, and half of such soils is alkaline. In such alkaline soils, iron is present in the form of trivalent ferric hydroxide ($Fe(OH)_3$), which is insoluble in water; plants are thus unable to sufficiently absorb iron from their roots, resulting in iron deficiency.

It is known that graminaceous plants, such as barley, rice, wheat, and corn, secrete from their roots mugineic acids (chelating agents), such as a mugineic acid represented by the following formula (A) and 2'-deoxymugineic acid (DMA) represented by the following formula (B), that the chelating agent forms a complex with iron to dissolve iron, and that the complex is taken into the plant body via a specific transporter.

(A)

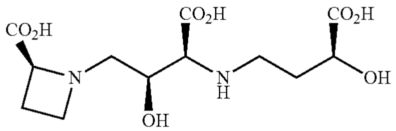

(B)

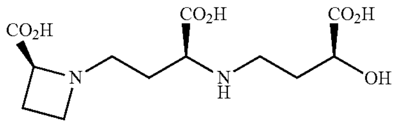

This makes it possible to absorb iron ions from alkaline soils. However, since the ability to secrete mugineic acids is typically low, there are also many graminaceous plants that cannot grow in alkaline soils, such as rice and corn.

Accordingly, the present inventors have proposed a heterocycle-containing amino acid compound useful as a chelating agent with iron uptake ability that can be supplied as a fertilizer in order to enable agriculture even in poor alkaline soils (Patent Literature (PTL) 1 and PTL 2).

CITATION LIST

Patent Literature

PTL 1: Japanese Patent No. 6347396
PTL 2: Japanese Patent No. 6744530

SUMMARY OF INVENTION

Technical Problem

The heterocycle-containing amino acid compound described in PTL 1 and PTL 2 are synthesized by a method comprising the following steps 1 to 4:

Step 1: oxidatively cleaving the vinyl group of a compound having a vinyl group at one end and an amino group protected by a protecting group at the other end to give an aldehyde, and reacting the aldehyde with a heterocycle-containing amino acid (reductive amination reaction);

Step 2: protecting the carboxyl group in the reaction product of step 1 and deprotecting the protecting group of the amino group;

Step 3: reacting the reaction product of step 2 with a compound having a formyl group at one end and a hydroxyl group protected by a protecting group at the other end; and Step 4: deprotecting the protecting group etc. of the hydroxyl group in the reaction product of step 3.

The above method requires four steps; however, if the synthesis is possible with a smaller number of steps using readily available starting materials, the industrial utility value of the method would be very high. Accordingly, a primary object of the present invention is to provide a simple method for producing a heterocycle-containing amino acid compound.

Solution to Problem

As a result of extensive research to achieve the above object, the present inventors have found that a heterocycle-containing amino acid compound can be simply produced by a method comprising the following steps A and B:

step (A) of reacting a compound represented by the following formula (2) or a salt thereof:

(2)

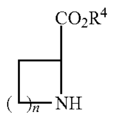

(wherein $R^4$ is a hydrogen atom or a carboxyl-protecting group, and n is an integer of 1 to 3), acrolein, a cyanating agent, and a compound represented by the following formula (3) or a salt thereof:

(3)

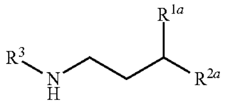

(wherein
$R^{1a}$ is a hydrogen atom or $CO_2R^{1b}$,
$R^{1b}$ is a hydrogen atom or a carboxyl-protecting group,
$R^{2a}$ is a hydrogen atom or $OR^{2b}$,
$R^{2b}$ is a hydrogen atom or a hydroxyl-protecting group, and
$R^3$ is a hydrogen atom or an amino-protecting group); and
step (B) of converting the cyano group of a compound represented by formula (1) or a salt thereof obtained in step A:

(1)

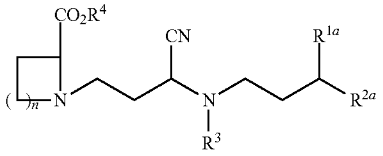

(wherein
$R^{1a}$ is a hydrogen atom or $CO_2R^{1b}$,
$R^{1b}$ is a hydrogen atom or a carboxyl-protecting group,
$R^{2a}$ is a hydrogen atom or $OR^{2b}$,
$R^2$ b is a hydrogen atom or a hydroxyl-protecting group,
$R^3$ is a hydrogen atom or an amino-protecting group,
$R^4$ is a hydrogen atom or a carboxyl-protecting group, and
n is as defined above),
into a carboxyl group by hydrolysis.

The present inventors have conducted further research based on this finding and completed the present invention.

The present invention encompasses the following embodiments.

Item 1.

A method for producing a compound represented by the following formula (1) or a salt thereof:

(1)

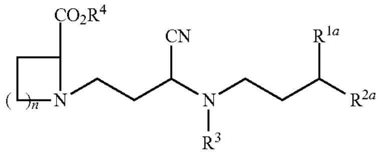

wherein
$R^{1a}$ is a hydrogen atom or $CO_2R^{1b}$,
$R^{1b}$ is a hydrogen atom or a carboxyl-protecting group,
$R^{2a}$ is a hydrogen atom or $OR^{2b}$,
$R^{2b}$ is a hydrogen atom or a hydroxyl-protecting group,
$R^3$ is a hydrogen atom or an amino-protecting group,
$R^4$ is a hydrogen atom or a carboxyl-protecting group, and
n is an integer of 1 to 3,
the method comprising
step A of reacting a compound represented by the following formula (2) or a salt thereof:

(2)

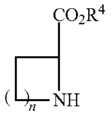

wherein $R^4$ and n are as defined above,
acrolein, a cyanating agent, and a compound represented by the following formula (3) or a salt thereof:

(3)

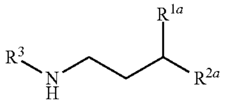

wherein $R^{1a}$, $R^{2a}$, and $R^3$ are as defined above.

Item 2.

A method for producing a compound represented by the following formula (4) or a salt thereof:

(4)

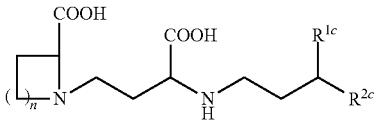

wherein
$R^{1c}$ is a hydrogen atom or a carboxyl group,
$R^{2c}$ is a hydrogen atom or a hydroxyl group, and
n is an integer of 1 to 3,
the method comprising
step B of converting the cyano group of a compound represented by the following formula (1) or a salt thereof:

(4)

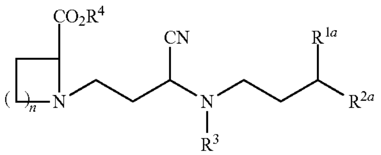

wherein
$R^{1a}$ is a hydrogen atom or $CO_2R^{1b}$,
$R^{1b}$ is a hydrogen atom or a carboxyl-protecting group,
$R^{2a}$ is a hydrogen atom or $OR^{2b}$,
$R^{2b}$ is a hydrogen atom or a hydroxyl-protecting group,
$R^3$ is a hydrogen atom or an amino-protecting group,
$R^4$ is a hydrogen atom or a carboxyl-protecting group, and
n is as defined above,
into a carboxyl group by hydrolysis.

Item 3.

The method according to Item 2, wherein the step B is performed in the presence of an acid.

Item 4.

The method according to Item 3, wherein the acid is an inorganic acid.

Item 5.

The method according to Item 3 or 4, wherein the acid is at least one member selected from the group consisting of hydrochloric acid, phosphoric acid, sulfuric acid, and nitric acid.

Item 6.

The method according to any one of Items 2 to 5, wherein the carboxyl-protecting group is an alkyl group, an alkenyl group, or an aralkyl group, the hydroxyl-protecting group is an alkyl group, an aralkyl group, a silyl group, or a trialkylsilyl group, and the amino-protecting group is an alkoxycarbonyl group, an alkenyloxycarbonyl group, or an aralkyloxycarbonyl group.

Item 7.

The method according to any one of Items 2 to 6, further comprising step A of reacting a compound represented by the following formula (2) or a salt thereof:

(2)

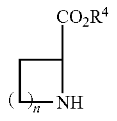

wherein $R^4$ and n are as defined above, acrolein, a cyanating agent, and a compound represented by the following formula (3) or a salt thereof:

(3)

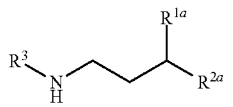

wherein $R^{1a}$, $R^{2a}$, and $R^3$ are as defined above, to obtain the compound represented by formula (1).

Item 8.

A compound represented by the following formula (1) or a salt thereof:

(1)

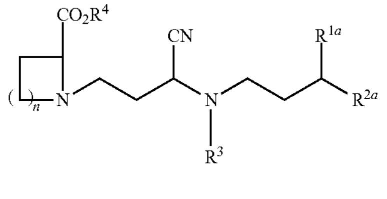

wherein $R^{1a}$ is a hydrogen atom or $CO_2R^{1b}$, $R^{1b}$ is a hydrogen atom or a carboxyl-protecting group, $R^{2a}$ is a hydrogen atom or $OR^{2b}$, $R^{2b}$ is a hydrogen atom or a hydroxyl-protecting group, $R^3$ is a hydrogen atom or an amino-protecting group, $R^4$ is a hydrogen atom or a carboxyl-protecting group, and n is an integer of 1 to 3.

Item 9.

The compound or a salt thereof according to Item 8, wherein the carboxyl-protecting group is an alkyl group, an alkenyl group, or an aralkyl group, the hydroxyl-protecting group is an alkyl group, an aralkyl group, a silyl group, or a trialkylsilyl group, and the amino-protecting group is an alkoxycarbonyl group, an alkenyloxycarbonyl group, or an aralkyloxycarbonyl group.

Advantageous Effects of Invention

The present invention provides a simple method for producing a heterocycle-containing amino acid compound.

DESCRIPTION OF EMBODIMENT

1. Definition

As used herein, "$C_{a-b}$" means that the number of carbon atoms in the subject is an integer of a or more and b or less.

As used herein, the term "protecting group" refers to a group used to protect a functional group from a specific chemical reaction.

As used herein, the term "carboxyl-protecting group" is a concept that encompasses protecting groups usually used to protect a carboxyl group in this field. For example, the concept encompasses all of the protecting groups etc. described in "Protective Groups in Organic Synthesis" (by T. W. Green and P. G. M. Wuts). Examples of the carboxyl-protecting group include an alkyl group optionally having one or more substituents, an alkenyl group optionally having one or more substituents, a cycloalkyl group optionally having one or more substituents, an aryl group optionally having one or more substituents, and an aralkyl group optionally having one or more substituents.

As used herein, the term "hydroxyl-protecting group" is a concept that encompasses protecting groups usually used to protect a hydroxyl group in this field. For example, the concept encompasses all of the protecting groups etc. described in "Protective Groups in Organic Synthesis" (by T. W. Green and P. G. M. Wuts). Examples of the hydroxyl-protecting group include an alkyl group optionally having one or more substituents, a cycloalkyl group optionally having one or more substituents, an aryl group optionally having one or more substituents, an aralkyl group optionally having one or more substituents, a 2-tetrahydropyranyl group optionally having one or more substituents, an alkylcarbonyl group optionally having one or more substituents, an arylcarbonyl group optionally having one or more substituents, an aralkylcarbonyl group optionally having one or more substituents, and a silyl group ($—SiH_3$) optionally having one or more substituents.

As used herein, the term "amino-protecting group" is a concept that encompasses protecting groups usually used to protect an amino group in this field. For example, the concept encompasses all of the protecting groups etc. described in "Protective Groups in Organic Synthesis" (by T. W. Green and P. G. M. Wuts). Examples of the amino-protecting group include an alkylcarbonyl group optionally having one or more substituents, an arylcarbonyl group optionally having one or more substituents, an aralkylcarbonyl group optionally having one or more substituents, an alkoxycarbonyl group optionally having one or more substituents, an alkenyloxycarbonyl group optionally having one or more substituents, an aryloxycarbonyl group optionally having one or more substituents, an aralkyloxycarbonyl group optionally having one or more substituents, an alkylsulfonyl group optionally having one or more substituents, and an arylsulfonyl group optionally having one or more substituents.

As used herein, the term "alkyl group" is a concept that encompasses linear alkyl groups and branched alkyl groups. Examples of alkyl groups include linear $C_{1-10}$ alkyl groups, such as a methyl group, an ethyl group, an n-propyl group, an n-butyl group, an n-pentyl group, and an n-hexyl group; and branched $C_{3-10}$ alkyl groups, such as an isopropyl group, an isobutyl group, an s-butyl group, a t-butyl group, an isopentyl group, a neopentyl group, an isohexyl group, an isoheptyl group, an isooctyl group, and a 2-ethylhexyl group.

As used herein, the term "alkenyl group" is a concept that encompasses linear alkenyl groups and branched alkenyl groups. Examples of alkenyl groups include linear $C_{1-10}$ alkenyl groups, such as a vinyl group, a 1-propenyl group, and an allyl group; and branched $C_{3-10}$ alkenyl groups, such as a 1-methylethenyl group and a 2-methyl-2 propenyl group.

As used herein, the term "cycloalkyl group" refers to a cyclic alkyl group. Examples of cycloalkyl groups include $C_{5-20}$ cycloalkyl groups, such as a cyclopentyl group and a cyclohexyl group.

As used herein, the term "aryl group" refers to a monovalent aromatic hydrocarbon group. Examples of aryl groups include $C_{6-20}$ aryl groups, such as a phenyl group and a naphthyl group.

As used herein, the term "aralkyl group" refers to an arylalkyl group. Examples of aralkyl groups include $C_{7-20}$ aryl groups, such as a benzyl group, a trityl group, and a phenethyl group.

As used herein, the term "alkylcarbonyl group" refers to a group represented by the formula: $R^A$—CO— (wherein $R^A$ is an alkyl group). Examples of alkylcarbonyl groups include $C_{1-10}$ alkylcarbonyl groups, such as a methylcarbonyl group (an acetyl group), an ethylcarbonyl group, a propylcarbonyl group (an n-propylcarbonyl group and isopropylcarbonyl group), and a butylcarbonyl group (an n-butylcarbonyl group, isobutylcarbonyl group, s-butylcarbonyl group, and t-butylcarbonyl group).

As used herein, the term "arylcarbonyl group" refers to a group represented by the formula: $R^B$—CO— (wherein $R^B$ is an aryl group). Examples of arylcarbonyl groups include $C_{6-20}$ arylcarbonyl groups, such as a benzoyl group and a naphthoyl group.

As used herein, the term "aralkylcarbonyl group" refers to a group represented by the formula: $R^C$—CO— (wherein $R^C$ is an aralkyl group). Examples of aralkylcarbonyl groups include $C_{7-20}$ aralkylcarbonyl groups, such as a benzylcarbonyl group and a phenethylcarbonyl group.

As used herein, the term "alkoxycarbonyl group" refers to a group represented by the formula: $R^D$—O—CO— (wherein $R^D$ is an alkyl group). Examples of alkoxycarbonyl groups include $C_{1-10}$ alkoxycarbonyl groups, such as a methoxycarbonyl group, an ethoxycarbonyl group, a propoxycarbonyl group (an n-propoxycarbonyl group and isopropoxycarbonyl group), and a butoxycarbonyl group (an n-butoxycarbonyl group, isobutoxycarbonyl group, s-butoxycarbonyl group, and t-butoxycarbonyl group).

As used herein, the term "alkenyloxycarbonyl group" refers to a group represented by the formula: $R^E$—O—CO— (wherein $R^E$ is an alkenyl group). Examples of alkenyloxycarbonyl groups include $C_{1-10}$ alkenyloxycarbonyl groups, such as a vinyloxycarbonyl group, an allyloxycarbonyl group, and a propenyloxycarbonyl group.

As used herein, the term "aryloxycarbonyl group" refers to a group represented by the formula: $R^F$—O—CO— (wherein $R^F$ is an aryl group). Examples of aryloxycarbonyl groups include $C_{6-20}$ aryloxycarbonyl groups, such as a phenyloxycarbonyl group and a naphthyloxycarbonyl group.

As used herein, the term "aralkyloxycarbonyl group" refers to a group represented by the formula: $R^G$—O—CO— (wherein $R^G$ is an aralkyl group). Examples of aralkyloxycarbonyl groups include $C_{7-20}$ aralkyloxycarbonyl groups, such as a benzyloxycarbonyl group, a 9-fluorenylmethyloxycarbonyl group, and a phenethyloxycarbonyl group.

As used herein, the term "alkylcarbonyloxy group" refers to a group represented by the formula: $R^H$—CO—O— (wherein $R^H$ is an alkyl group). Examples of the alkylcarbonyloxy group include $C_{1-10}$ alkylcarbonyloxy groups, such as an acetyloxy group, a propionyloxy group (an n-propionyloxy group and isopropionyloxy group), and a butyryloxy group (an n-butyryloxy group, isobutyryloxy group, s-butyryloxy group, and t-butyryloxy group).

As used herein, the term "alkylsulfonyl group" refers to a group represented by the formula: $R^I$—$SO_2$— (wherein $R^I$ is an alkyl group). Examples of alkylsulfonyl groups include $C_{1-10}$ alkylsulfonyl groups, such as a methylsulfonyl group and an ethylsulfonyl group.

As used herein, the term "arylsulfonyl group" refers to a group represented by the formula: $R^J$—$SO_2$— (wherein $R^J$ is an aryl group). Examples of arylsulfonyl groups include $C_{6-20}$ arylsulfonyl groups, such as a phenylsulfonyl group and a naphthylsulfonyl group.

As used herein, the term "substituent" refers to an atom or an atomic group that replaces a hydrogen atom in the substitution target. Examples of substituents include, but are not limited to, a halogen atom, a nitro group, an alkoxy group, and an alkylcarbonyloxy group.

As used herein, the term "halogen atom" is a concept that encompasses a fluorine atom, a chlorine atom, a bromine atom, and an iodine atom.

As used herein, the term "alkoxy group" refers to a group represented by the formula: $R^K$O— (wherein $R^K$ is an alkyl group). Examples of alkoxy groups include $C_{1-10}$ alkoxy groups, such as a methoxy group, an ethoxy group, a propoxy group (an n-propoxy group and isopropoxy group), and a butoxy group (an n-butoxy group, isobutoxy group, s-butoxy group, and t-butoxy group).

Specific examples of an alkyl group having one or more substituents include $C_{1-6}$ alkoxy $C_{1-6}$ alkyl groups, such as a methoxymethyl group and an ethoxyethyl group; $C_{1-6}$ alkoxy $C_{1-6}$ alkoxy $C_{1-6}$ alkyl groups, such as a methoxyethoxymethyl group; and $C_{1-6}$ alkylcarbonyloxy $C_{1-6}$ alkyl groups, such as an acetoxymethyl group, an acetoxyethyl group, a propionyloxymethyl group, an n-butyryloxymethyl group, an isobutyryloxymethyl group, and a pivaloyloxymethyl group.

Specific examples of an aralkyl group having one or more substituents include nitroaralkyl groups, such as an o-, m-, or p-nitrobenzyl group and a 2,4-dinitrobenzyl group; haloaralkyl groups, such as a p-chlorobenzyl group and a p-bromobenzyl group; and $C_{1-6}$ alkoxyaralkyl groups, such as a p-methoxybenzyl group.

Specific examples of a silyl group having one or more substituents include trialkylsilyl groups and alkyldiarylsilyl groups. Examples of trialkylsilyl groups include tri $C_{1-6}$ alkylsilyl groups, such as a trimethylsilyl (TMS) group, a triethylsilyl (TES) group, a triisopropylsilyl (TIPS) group, and a t-butyldimethylsilyl (TBS) group. Examples of alkyldiarylsilyl groups include $C_{1-6}$ alkyl di $C_{6-12}$ arylsilyl groups, such as a t-butyldiphenylsilyl (TBDPS) group.

2. Compound Represented By Formula (1) or Salt Thereof

A compound represented by formula (1) or a salt thereof is an intermediate useful for producing a compound represented by formula (4) or a salt thereof.

$R^{1a}$ is a hydrogen atom or $CO_2R^{1b}$, and $R^{1b}$ is a hydrogen atom or a carboxyl-protecting group. $R^{1b}$ is preferably a carboxyl-protecting group, more preferably an alkyl group, an alkenyl group, or an aralkyl group, and still more preferably a $C_{1-6}$ alkyl group, such as a methyl group, an ethyl group, or a t-butyl group; a $C_{2-6}$ alkenyl group, such as an allyl group; or a $C_{7-20}$ aralkyl group, such as a benzyl group or a trityl group.

$R^{2a}$ is a hydrogen atom or $OR^{2b}$, and $R^{2b}$ is a hydrogen atom or a hydroxyl-protecting group. $R^{2b}$ is preferably a hydroxyl-protecting group, more preferably an alkyl group, an aralkyl group, a silyl group, or a trialkylsilyl group, and still more preferably a $C_{1-6}$ alkyl group, such as a methyl group, an ethyl group, or a t-butyl group; a $C_{7-20}$ aralkyl group, such as a benzyl group; a silyl group; or a tri $C_{1-6}$ alkylsilyl group, such as a TMS group, a TIPS group, or a TBS group.

$R^3$ is a hydrogen atom or an amino-protecting group. $R^3$ is preferably an amino-protecting group, more preferably an alkoxycarbonyl group, an alkenyloxycarbonyl group, or an aralkyloxycarbonyl group, and still more preferably a $C_{1-6}$ alkoxycarbonyl group, such as a t-butoxycarbonyl group; a $C_{2-6}$ alkenyloxycarbonyl group, such as an allyloxycarbonyl group; or a $C_{7-20}$ aralkyloxycarbonyl group, such as a benzyloxycarbonyl group or a 9-fluorenylmethyloxycarbonyl group.

$R^4$ is a hydrogen atom or a carboxyl-protecting group. $R^4$ is preferably a carboxyl-protecting group, more preferably an alkyl group, an alkenyl group, or an aralkyl group, and still more preferably a $C_{1-6}$ alkyl group, such as a methyl group, an ethyl group, or a t-butyl group; a $C_{2-6}$ alkenyl group, such as an allyl group; or a $C_{7-20}$ aralkyl group, such as a benzyl group or a trityl group.

The combination of $R^{1a}$, $R^{2a}$, $R^3$, and $R^4$ is preferably a combination in which $R^{1a}$ is a hydrogen atom or $CO_2R^{1b}$, $R^{1b}$ is a carboxyl-protecting group, $R^{2a}$ is a hydrogen atom or $OR^{2b}$, $R^{2b}$ is a hydroxyl-protecting group, $R^3$ is a hydrogen atom, and $R^4$ is a carboxyl-protecting group. In one embodiment, it is preferred that $R^{1a}$ is $CO_2R^{1b}$, $R^{1b}$ is a carboxyl-protecting group, $R^{2a}$ is $OR^{2b}$, $R^{2b}$ is a hydroxyl-protecting group, $R^3$ is a hydrogen atom, and $R^4$ is a carboxyl-protecting group. In another embodiment, it is preferred that $R^{1a}$ is $CO_2R^{1b}$, $R^{1b}$ is a carboxyl-protecting group, $R^{2a}$ is a hydrogen atom, $R^3$ is a hydrogen atom, and $R^4$ is a carboxyl-protecting group. In another embodiment, it is preferred that $R^{1a}$ is a hydrogen atom, $R^{2a}$ is $OR^{2b}$, $R^{2b}$ is a hydroxyl-protecting group, $R^3$ is a hydrogen atom, and $R^4$ is a carboxyl-protecting group.

n is an integer of 1 to 3.

The salt of the compound represented by formula (1) may be any salt. Examples of such salts include inorganic acid salts, such as hydrochloride, sulfate, and nitrate; carboxylic acid salts, such as acetate, trifluoroacetate, oxalate, and benzoate; organic acid salts, such as sulfonate (e.g., methanesulfonate and p-toluenesulfonate); alkali metal salts, such as sodium salts and potassium salts; alkaline earth metal salts, such as magnesium salts and calcium salts; and ammonium salts, such as dimethylammonium and triethylammonium. The salt is preferably an inorganic acid salt, and more preferably hydrochloride.

The compound represented by formula (1) or a salt thereof includes optical isomers, such as enantiomers and diastereomers, and racemates.

3. Method for Producing Compound Represented By Formula (1) or Salt Thereof

In one embodiment, the method for producing a compound represented by formula (1) or a salt thereof comprises step A of reacting a compound represented by formula (2) or a salt thereof, acrolein, a cyanating agent, and a compound represented by formula (3) or a salt thereof.

$R^4$ and n in formula (2) are as described for formula (1). Either of the compound represented by formula (2) or a salt thereof may be used. The salt of the compound represented by formula (2), when used, may be any salt, and examples thereof include the same salts as those listed as examples of the salt of the compound represented by formula (1). If the salt affects the reaction, desalting is preferably performed before use.

The amount of acrolein for use is, for example, 0.1 mol or more, preferably 0.5 mol or more, and more preferably 1 mol or more, per mole of the compound represented by formula (2) or a salt thereof. The amount of acrolein for use is, for example, 5 mol or less, preferably 4 mol or less, more preferably 3 mol or less, and still more preferably 2 mol or less, per mole of the compound represented by formula (2) or a salt thereof.

Examples of the cyanating agent include hydrogen cyanide; alkali metal cyanides, such as sodium cyanide and potassium cyanide; and cyanating organic reagents, such as trimethylsilyl cyanide and acetone cyanohydrin. The amount of the cyanating agent for use is, for example, 0.1 mol or more, preferably 0.5 mol or more, and more preferably 1 mol or more, per mole of the compound represented by formula (2) or a salt thereof. The amount of the cyanating agent for use is, for example, 5 mol or less, preferably 4 mol or less, more preferably 3 mol or less, and still more preferably 2 mol or less, per mole of the compound represented by formula (2) or a salt thereof.

$R^{1a}$, $R^{2a}$, and $R^3$ in formula (3) are as described for formula (1). Either of the compound represented by formula (3) or a salt thereof may be used. The salt of the compound represented by formula (3), when used, may be any salt, and examples thereof include the same salts as those listed as examples of the salt of the compound represented by formula (1). If the salt affects the reaction, desalting is preferably performed before use. The amount of the compound represented by formula (3) or a salt thereof for use is, for example, 0.1 mol or more, preferably 0.5 mol or more, and more preferably 1 mol or more, per mole of the compound represented by formula (2) or a salt thereof. The amount of the compound represented by formula (3) or a salt thereof for use is, for example, 5 mol or less, preferably 4 mol or less, more preferably 3 mol or less, and still more preferably 2 mol or less, per mole of the compound represented by formula (2) or a salt thereof.

The reaction of the compound represented by formula (2) or a salt thereof, acrolein, a cyanating agent, and the compound represented by formula (3) or a salt thereof usually proceeds by mixing these components. The order of mixing may be any order; the reaction proceeds regardless of the order of mixing. An example of the mixing method includes a method in which the compound represented by formula (2) or a salt thereof is mixed with acrolein, the resulting mixture is then mixed with the compound represented by formula (3) or a salt thereof, and the resulting mixture is finally mixed with a cyanating agent (this method is referred to below as "mixing method 1"). Another example is a method in which a mixture of the compound represented by formula (2) or a salt thereof and acrolein is mixed with a mixture of the compound represented by formula (3) and a cyanating agent (this method is referred to below as "mixing method 2"). Still another example is a method in which the compound represented by formula (2) or a salt thereof, acrolein, a cyanating agent, and the compound represented by formula (3) or a salt thereof are mixed all together (this method is referred to below as "mixing method 3").

Step A is usually performed in the presence of a solvent. The solvent may be a polar solvent or a nonpolar solvent. Examples of polar solvents include water; halogenated hydrocarbons, such as methylene chloride; alcohols, such as isopropanol; ethers, such as tetrahydrofuran and dioxane; and nitriles, such as acetonitrile. Examples of nonpolar solvents include aromatic hydrocarbons, such as toluene. The solvents may be used alone or in a combination of two or more. The solvent is preferably a polar solvent, and more preferably an ether, such as tetrahydrofuran.

Step A can be performed in the absence or presence of a base. For example, when step A is performed at a low temperature such as −15° C. or lower, or when the compound represented by formula (2) or a salt thereof is mixed with acrolein, step A is preferably performed in the presence of a base. Examples of the base include triethylamine (TEA), diisopropylethylamine (DIPEA), tetramethylguanidine (TMG), diazabicyclooctane (DABCO), diazabicyclononene (DBN), diazabicycloundecene (DBU), triazabicyclodecene (TBD), N-methyl-triazabicyclodecene (MTBD), pyridine, and 4-dimethylaminopyridine (DMAP). The bases may be used alone or in a combination of two or more.

The amount of the base for use is, for example, 0.005 mol or more, and preferably 0.01 mol or more, per mole of the compound represented by formula (2) or a salt thereof. The amount of the base for use is, for example, 0.1 mol or less, and preferably 0.05 mol or less, per mole of the compound represented by formula (2) or a salt thereof.

Step A can be performed in the absence or presence of an acid. Examples of the acid include, but are not limited to, aliphatic carboxylic acids, such as acetic acid, trifluoroacetic acid, and pivalic acid; aromatic carboxylic acids, such as benzoic acid; and sulfonic acids, such as tosic acid. The acids may be used alone or in a combination of two or more. The acid is preferably an aliphatic carboxylic acid, such as acetic acid or trifluoroacetic acid.

The amount of the acid for use is, for example, 0.005 mol or more, preferably 0.01 mol or more, and more preferably 0.02 mol or more, per mole of the compound represented by formula (2) or a salt thereof. The amount of the acid for use is, for example, 5 mol or less, preferably 3 mol or less, and more preferably 1 mol or less per mole of the compound represented by formula (2) or a salt thereof.

The reaction temperature may be any temperature at which the reaction proceeds. The reaction temperature is, for example, −100° C. or higher, preferably −90° C. or higher, and more preferably −80° C. or higher. When the four components are mixed all together as in mixing method 3, the reaction temperature may be set at room temperature, for example, in the range of 5 to 35° C. On the other hand, when the four components are mixed in a predetermined order as in mixing methods 1 and 2, the mixing of the compound represented by formula (2) or a salt thereof with acrolein may be performed at, for example, −15° C. or lower, preferably −30° C. or lower, more preferably −40° C. or lower, and still more preferably −50° C. or lower; and the other mixing may be performed at room temperature, for example, in the range of 5 to 35° C.

The method for producing the compound represented by formula (1) or a salt thereof may further comprise a purification step, in addition to step A. Examples of purification methods include filtration, extraction, concentration, chromatography, or a combination thereof. Further, the method for producing the compound represented by formula (1) or a salt thereof may further comprise an optical resolution step, in addition to step A.

4. Compound Represented By Formula (4) or Salt Thereof $R^{1c}$ is a hydrogen atom or a carboxyl group, and $R^{2c}$ is a hydrogen atom or a hydroxyl group. The combination of $R^{1c}$ and $R^{2c}$ is preferably a combination in which $R^{1c}$ is a carboxyl group, and $R^{2c}$ is a hydroxyl group, a combination in which $R^{1c}$ is a carboxyl group, and $R^{2c}$ is a hydrogen atom, or a combination in which $R^{1c}$ is a hydrogen atom, and $R^{2c}$ is a hydroxyl group.

n is an integer of 1 to 3.

The salt of the compound represented by formula (4) may be any salt, and examples thereof include the same salts as those listed as examples of the salt of the compound represented by formula (1).

5. Method for Producing Compound Represented By Formula (4) or Salt Thereof

In one embodiment, the method for producing a compound represented by formula (4) or a salt thereof comprises step B of converting the cyano group of the compound represented by formula (1) or a salt thereof into a carboxyl group by hydrolysis.

The method for hydrolyzing a cyano group may be any method; usually, hydrolysis is performed with an acid. Examples of the acid include inorganic acids, such as hydrochloric acid, phosphoric acid, sulfuric acid, and nitric acid. The acids may be used alone or in a combination of two or more. The amount of the acid for use is, for example, 1 mol or more, preferably 2 mol or more, and more preferably 3 mol or more, per mole of the compound represented by formula (4) or a salt thereof. The amount of the acid for use is, for example, 100 mol or less, preferably 50 mol or less, and more preferably 30 mol or less, per mole of the compound represented by formula (4) or a salt thereof.

The reaction temperature of the hydrolysis may be any temperature at which the reaction proceeds. The reaction temperature is, for example, 80° C. or higher, preferably 90° C. or higher, and more preferably 100° C. or higher. The reaction temperature is, for example, 150° C. or lower, preferably 140° C. or lower, and more preferably 130° C. or lower.

Depending on the type, the protecting groups are removed simultaneously with the hydrolysis reaction in step B. However, a step of removing (deprotecting) protecting groups may be further provided for protecting groups that are not removed in the hydrolysis reaction in step B. The deprotection method can be appropriately selected according to the type of protecting groups. For example, a reference can be made to "Protective Groups in Organic Synthesis" (by T. W. Green and P. G. M. Wuts).

The method for producing the compound represented by formula (4) or a salt thereof preferably further comprises step A, in addition to step B. Further, the method for producing the compound represented by formula (4) or a salt thereof may further comprise a purification step. Examples of purification methods include filtration, extraction, concentration, chromatography, recrystallization, and a combination thereof. The method for producing the compound represented by formula (4) or a salt thereof may further comprise an optical resolution step.

EXAMPLES

The present invention is described in detail below based on Examples; however, the present invention is not limited by these Examples. The abbreviations in the Examples have the following meanings.

tBu: tertiary butyl

THF: tetrahydrofuran $Et_2O$: diethyl ether

DBU: diazabicycloundecene

TFA: trifluoroacetic acid

TMSCN: trimethylsilylcyanide iPrOH: isopropanol

Example 1

Synthesis of t-Butyl(3-cyano-3-(((S)-3,4-di-t-butoxy-4-oxobutyl)amino)propyl)-L-prolinate (4) (Method 1)

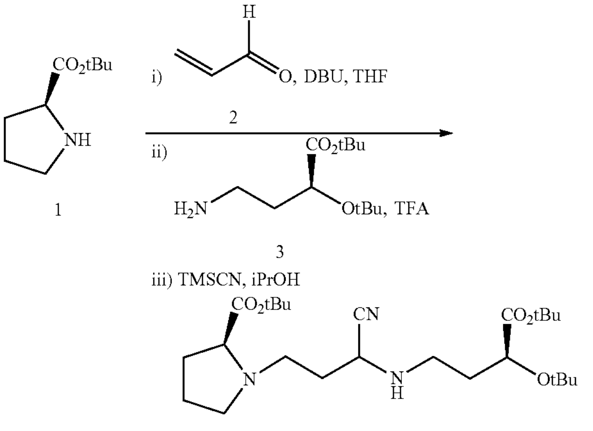

4 tBu proline (1) (59 mg, 0.34 mmol) was dissolved in THF (1.2 mL). DBU (0.1 M THF solution) (0.17 mL, 0.017 mmol) was added thereto and cooled to −78° C. Acrolein (2) (25 μL, 0.34 mmol) was added to the reaction solution, and the mixture was stirred at −78° C. for 2 hours. A tBu-aminobutyric acid solution (obtained by dissolving tBu-aminobutyric acid (3) (79 mg, 0.34 mmol) in THF (0.5 mL)) and a 0.1 M THF solution (34 μL, 0.0034 mmol) of TFA were added to the reaction solution, and the mixture was stirred at −78° C. for 2 hours. Subsequently, TMSCN (51 μL, 0.41 mmol) and iPrOH (31 μL, 0.41 mmol) were added, and the mixture was stirred for 2 hours. After completion of the reaction, the resulting product was diluted with $Et_2O$, and then a saturated aqueous $NaHCO_3$ solution was added. The mixture was extracted with $Et_2O$, and the organic phase was dried over $MgSO_4$, filtered, and concentrated (NMR yield: 80%). The concentrated residue was purified by column chromatography (n-hexane/ethyl acetate (4:1)) to give a title compound (4) of a yellow liquid (108 mg, 68%).

Example 2

Synthesis of t-Butyl(3-cyano-3-(((S)-3,4-di-t-butoxy-4-oxobutyl)amino)propyl)-L-prolinate (4) (Method 2)

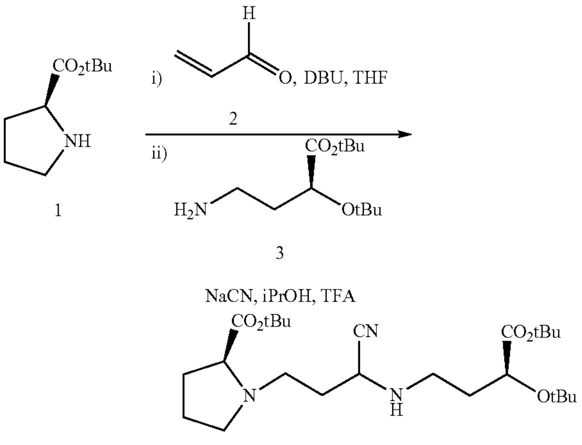

4 tBu proline (1) (123 mg, 0.71 mmol) was dissolved in THF (3.6 mL). DBU (5 μL, 0.035 mmol) was added thereto and cooled to −78° C. Acrolein (2) (53 μL, 0.71 mmol) was added to the reaction solution, and the mixture was stirred at −78° C. for 2 hours. A previously prepared tBu-aminobutyric acid solution (obtained by adding NaCN (42 mg, 0.85 mmol) and TFA (66 μL, 0.85 mmol) to an iPrOH (3 mL) solution of tBu-aminobutyric acid (3) (167 mg, 0.72 mmol), and stirring the mixture at room temperature for hours) was added to the reaction solution, and the mixture was stirred at −78° C. for 2 hours. After completion of the reaction, the resulting product was diluted with $Et_2O$, and then a saturated aqueous $NaHCO_3$ solution was added. The mixture was extracted with $Et_2O$, and the organic phase was dried over $MgSO_4$, filtered, and concentrated to give the title compound (4) (NMR yield: 55%).

$^1H$ NMR (400 MHz, $CD_3OD$): 4.10 (dd, J=4.4, 8.4 Hz, 1H), 4.06 (dd, J=5.3, 7.2 Hz, 1H), 3.85 (t, J=6.5 Hz, 1H), 3.80 (dd, J=6.4, 7.3 Hz, 1H), 3.19-3.14 (m, 1H), 3.09-3.04 (m, 1H), 2.96-2.85 (m, 2H), 2.07-2.54 (m, 2H), 2.34 (ddd, J=8.0, 12.4, 16 Hz, 1H), 2.15-2.06 (m, 1H), 2.01-1.74 (m, 7H), 1.48 (s, 18H), 1.99 (s, 9H)

Example 3

Synthesis of (3-Carboxy-3-(((S)-3-carboxy-3-hydroxypropyl)amino)propyl)-L-proline (5)

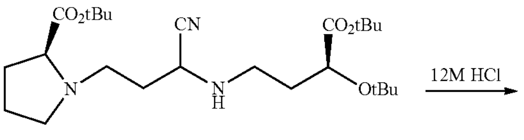

4

-continued

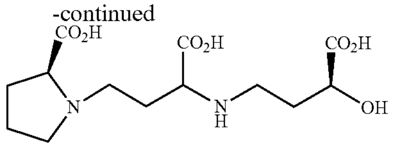

5

A 12 M aqueous hydrochloric acid solution (5 mL) was added to compound (4) (474 mg, 1.01 mmol), and the mixture was stirred at 0° C. for 30 minutes. Thereafter, the reaction solution was heated to room temperature and further stirred for 1 hour. Thereafter, the reaction solution was heated to 100° C. and stirred for 19 hours. The solution was cooled to room temperature and then concentrated under reduced pressure. The concentrated residue was dissolved in $H_2O$ (1.5 mL), activated carbon (100 mg) was added thereto, and the mixture was stirred at room temperature for 5 minutes. The resulting solution was filtered and the filtrate was concentrated. The resulting residue was purified with an ion exchange resin ($H_2O$→5% $NH_3$) to give a title compound (5) of a brown solid (214.6 mg, 70%).

$^1H$ NMR (500 MHz, $D_2O$): 4.43 (dd, J=4.3, 8.1 Hz, 1H), 4.20 (td, J=5.5, 9.6 Hz, 1H), 3.96 (dd, J=4.4, 8.6 Hz, 1H), 3.91 (t, J=6.7 Hz, 1H), 3.82 (ddd, J=3.7, 7.2, 11 Hz, 1H), 3.60-3.37 (m, 2H), 3.34-3.18 (m, 3H), 2.56-2.50 (m, 1H), 2.37-2.26 (m, 3H), 2.23-1.95 (m, 4H)

The invention claimed is:

1. A method for producing a compound represented by the following formula (1) or a salt thereof:

(1)

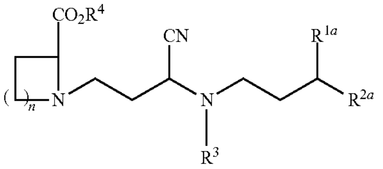

wherein $R^{1a}$ is a hydrogen atom or $CO_2R^{1b}$, $R^{1b}$ is a hydrogen atom or a carboxyl-protecting group, $R^{2a}$ is a hydrogen atom or $OR^{2b}$, $R^{2b}$ is a hydrogen atom or a hydroxyl-protecting group, $R^3$ is a hydrogen atom or an amino-protecting group, $R^4$ is a hydrogen atom or a carboxyl-protecting group, and n is an integer of 1 to 3, the method comprising step A of reacting a compound represented by the following formula (2) or a salt thereof:

(2)

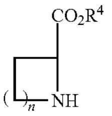

wherein $R^4$ and n are as defined above, acrolein, a cyanating agent, and a compound represented by the following formula (3) or a salt thereof:

(3)

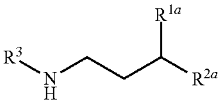

wherein $R^{1a}$, $R^{2a}$, and $R^3$ are as defined above.

2. A method for producing a compound represented by the following formula (4) or a salt thereof:

(4)

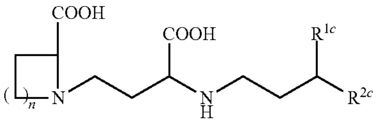

wherein $R^{1c}$ is a hydrogen atom or a carboxyl group, $R^{2c}$ is a hydrogen atom or a hydroxyl group, and n is an integer of 1 to 3, the method comprising step B of converting the cyano group of a compound represented by the following formula (1) or a salt thereof:

(1)

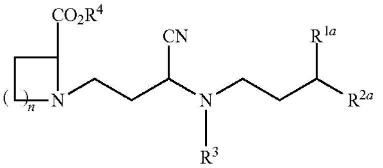

wherein $R^{1a}$ is a hydrogen atom or $CO^2R^{1b}$, $R^{1b}$ is a hydrogen atom or a carboxyl-protecting group, $R^{2a}$ is a hydrogen atom or $OR^{2b}$, $R^{2b}$ is a hydrogen atom or a hydroxyl-protecting group, $R^3$ is a hydrogen atom or an amino-protecting group, $R^4$ is a hydrogen atom or a carboxyl-protecting group, and n is as defined above, into a carboxyl group by hydrolysis.

3. The method according to claim 2, wherein the step B is performed in the presence of an acid.

4. The method according to claim 3, wherein the acid is an inorganic acid.

5. The method according to claim 3, wherein the acid is at least one member selected from the group consisting of hydrochloric acid, phosphoric acid, sulfuric acid, and nitric acid.

6. The method according to claim 2, wherein the carboxyl-protecting group is an alkyl group, an alkenyl group, or an aralkyl group, the hydroxyl-protecting group is an alkyl group, an aralkyl group, a silyl group, or a trialkylsilyl group, and the amino-protecting group is an alkoxycarbonyl group, an alkenyloxycarbonyl group, or an aralkyloxycarbonyl group.

7. The method according to claim 2, further comprising step A of reacting a compound represented by the following formula (2) or a salt thereof:

(2)

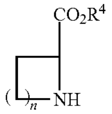

wherein $R^4$ and n are as defined above, acrolein, a cyanating agent, and a compound represented by the following formula (3) or a salt thereof:

(3)

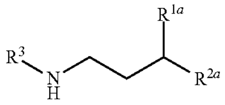

wherein $R^{1a}$, $R^{2a}$, and $R^3$ are as defined above, to obtain the compound represented by formula (1).

8. A compound represented by the following formula (1) or a salt thereof:

(1)

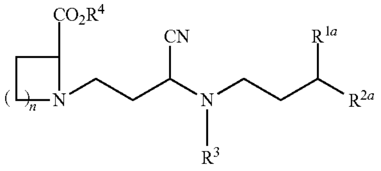

wherein $R^{1a}$ is a hydrogen atom or $CO_2R^{1b}$, $R^{1b}$ is a hydrogen atom or a carboxyl-protecting group, $R^{2a}$ is a hydrogen atom or $OR^{2b}$, $R^{2b}$ is a hydrogen atom or a hydroxyl-protecting group, $R^3$ is a hydrogen atom or an amino-protecting group, $R^4$ is a hydrogen atom or a carboxyl-protecting group, and n is an integer of 1 to 3.

9. The compound or a salt thereof according to claim 8, wherein the carboxyl-protecting group is an alkyl group, an alkenyl group, or an aralkyl group, the hydroxyl-protecting group is an alkyl group, an aralkyl group, a silyl group, or a trialkylsilyl group, and the amino-protecting group is an alkoxycarbonyl group, an alkenyloxycarbonyl group, or an aralkyloxycarbonyl group.

* * * * *